(12) United States Patent
Joseph et al.

(10) Patent No.: US 12,336,858 B2
(45) Date of Patent: Jun. 24, 2025

(54) METHODS FOR IDENTIFYING THE BOUNDARIES OF A BLOOD VESSEL

(71) Applicants: Healthcare Technology Innovation Centre, Chennai (IN); Indian Institute of Technology Madras (IIT Madras), Chennai (IN)

(72) Inventors: Jayaraj Joseph, Chennai (IN); Raj Kiran Vangapandu, Chennai (IN); Nabeel Pilaparambil Mashood, Chennai (IN); Mohanasankar Sivaprakasam, Chennai (IN)

(73) Assignees: HEALTHCARE TECHNOLOGY INNOVATION CENTRE, Chennai (IN); INDIAN INSTITUTE OF TECHNOLOGY MADRAS (IIT MADRAS), Chennai (IN)

( * ) Notice: Subject to any disclaimer, the term of this patent is extended or adjusted under 35 U.S.C. 154(b) by 209 days.

(21) Appl. No.: 17/996,722

(22) PCT Filed: Apr. 27, 2021

(86) PCT No.: PCT/IN2021/050411
§ 371 (c)(1),
(2) Date: Oct. 20, 2022

(87) PCT Pub. No.: WO2021/220300
PCT Pub. Date: Nov. 4, 2021

(65) Prior Publication Data
US 2023/0210497 A1     Jul. 6, 2023

(30) Foreign Application Priority Data
Apr. 27, 2020 (IN) ............................ 202041017854

(51) Int. Cl.
*A61B 8/00* (2006.01)

(52) U.S. Cl.
CPC .............. *A61B 8/44* (2013.01); *A61B 8/5207* (2013.01)

(58) Field of Classification Search
CPC ....... A61B 8/0858; A61B 8/0891; A61B 8/44; A61B 8/5207; G01S 7/52026; G01S 7/52036
See application file for complete search history.

(56) References Cited

U.S. PATENT DOCUMENTS

2003/0009101 A1*   1/2003   Sunagawa ............ A61B 8/0858
                                                                600/437
2008/0051660 A1*   2/2008   Kakadaris .............. A61B 8/488
                                                                600/454

(Continued)

*Primary Examiner* — Ashley K Buran
*Assistant Examiner* — Maria Christina Talty

(57) ABSTRACT

Embodiments of the present disclosure are directed to a vessel-wall-monitoring device (100) and a method for identifying the walls of blood vessel in a body. The method includes receiving, by the vessel-wall-monitoring device (100), a plurality of ultrasound echo signals from a transducer, wherein the plurality of ultrasound echo signals are transmitted to the transducer from locations of the blood vessel, extracting at least two consecutive ultrasound frames from the plurality of ultrasound echo signals, determining a shift between the at least two consecutive ultrasound frames by comparing samples of the at least two consecutive ultrasound frames, and identifying, a proximal wall and a distal wall of the blood vessel based on the shift between the at least two consecutive ultrasound frames.

16 Claims, 6 Drawing Sheets

(56) References Cited

U.S. PATENT DOCUMENTS

| | | | | |
|---|---|---|---|---|
| 2009/0163811 A1* | 6/2009 | Fukumoto | ............ | A61B 8/0858 |
| | | | | 600/443 |
| 2014/0249423 A1* | 9/2014 | Cai | ............ | A61B 8/12 |
| | | | | 600/463 |
| 2018/0014810 A1* | 1/2018 | Chen | ............ | A61B 8/5246 |
| 2018/0203103 A1* | 7/2018 | Pellegretti | ............ | G01S 15/8977 |

* cited by examiner

METHODS FOR IDENTIFYING THE BOUNDARIES OF A BLOOD VESSEL

PRIORITY DETAILS

The present application is based on, and claims priority from International Application PCT/IN2021/050411 filed 27 Apr. 2021 and Indian Application No. 202041017854 filed on 27 Apr. 2020, the disclosures of which are hereby incorporated by reference herein.

TECHNICAL FIELD

The present disclosure relates to medical monitoring and analysis, and more particularly to identifying walls of blood vessels in a body. The disclosure of which is hereby incorporated by reference herein

BACKGROUND

Arterial lumen diameter and wall thickness (assessed as intima-media thickness) constitute important sub-clinical measurements of cardiovascular risks. Several multicentre clinical studies and meta-data analyses have provided outcomes that recommend these measures as established surrogates and independent markers of various cardiovascular events, pathologies, and disease progression. Simultaneous measurement of their instantaneous values can help furnish several functional and material properties of the blood vessels. These properties include the distensibility (or compliance), stiffness index, modulus of elasticity, local pulse wave velocity and its variation within a cardiac cycle, viscoelasticity, wall-buffering function, endothelial dysfunction, central blood pressure, etc.

The non-invasive measurement of arterial diameter or wall thickness and their changes is performed using imaging technologies traditionally. This involves two tasks, the first of which is a localization or identification of vessel wall echoes which is a high-level task and the second is tracking them over time. These tasks are technically challenging and manually tedious, and thereby need further attention. Automation of both of these tasks is non-trivial, among which the localization or identification task is considered as a high-level task requiring intelligence.

However as the method's accuracy is implicit, it is also desirable if the measurements are yielded real-time and in automated or semi-automated fashion. Such methods that depend minimally on the operator are likely to reduce the time consumed for the measurement procedure and contribute towards better repeatability. This is particularly important to accelerate large scale studies or field-level screening, and also in settings with resource-constraints. Recent works have reviewed several automated and semi-automated techniques that employ segmentation on B-mode ultrasound images to evaluate the diameter and wall thickness. These state-of-the-art B-mode techniques meet the necessary clinical standards and requirements concerning the measurement of the artery's dimensional parameters. However, these modalities are expensive, and the advanced features required for performing such measurements are not augmented to the entry-level devices. Additionally, they are non-scalable, demand a skilled operator, and do not cater to out-of-clinic applications. In the context of India, the legal constraints imposed by the Pre-Natal Diagnostic Techniques (PNDT) act restrict imaging ultrasound devices to be deployed to the field, unless otherwise with special approvals. This has affected the ready availability of these ultrasound technologies to the rural sector of India, where the resources are scarce, both in terms of manpower and machinery.

In light of the above, there is a need to overcome the above stated disadvantages

SUMMARY

Embodiments of the present disclosure are directed to a system and methods in time domain and frequency domain for identifying a vessel in a human body. Each method features a method for automated identification of vascular boundaries, which features inspection of misalignment in echoes from each structure present in the consecutive ultrasound frames, exploiting the degree of misalignment in the independent echoes to identify the dynamic ones, identifying the echoes of interest from the pool of dynamic echoes, exhibiting the specific characteristic motion and providing robustness against false identification of other dynamic structures adjacent to the target vessel.

Embodiments of the present disclosure are directed to a method for identifying boundaries of a blood vessel in a human body. The method includes receiving, by a vessel-wall-monitoring device, a plurality of ultrasound echo signals from a transducer, wherein the plurality of ultrasound echo signals are transmitted to the transducer from locations of the blood vessel, continuously extracting, by the vessel-wall-monitoring device, at least two consecutive ultrasound frames from the plurality of ultrasound echo signals, comparing, by the vessel-wall-monitoring device, samples of the at least two consecutive ultrasound frames to determine a shift wherein the shift comprises determining at least one of a delay waveform and a phase change waveform between the at least two consecutive ultrasound frames, determining, by the vessel-wall-monitoring device, at least two adjacent extrema of at least one of the delay waveform and the phase change waveform, and identifying, by the vessel-wall-monitoring device, a proximal wall and a distal wall of the blood vessel based on the at least two adjacent extrema.

Another embodiment of the present disclosure is directed to an ultrasound frame being a digitized data frame of the ultrasound echo signal with a finite number of samples.

Another embodiment of the present disclosure is directed to the proximal wall and the distal wall of the blood vessel of the subject moving in opposite directions.

Another embodiment of the present disclosure is directed to identifying a proximal wall and a distal wall of the blood vessel based on the adjacent extrema by determining the at least two adjacent extrema to have opposing signs and magnitudes of the at least two adjacent extrema to be above a predefined threshold.

Another embodiment of the present disclosure is directed to comparing samples of the at least two consecutive ultrasound frames to determine a delay waveform between the at least two consecutive ultrasound frames. This includes comparing samples of the at least two consecutive ultrasound frames to determine an alignment dissimilarity between the at least two ultrasound frames, generating a two dimensional alignment error matrix based on the alignment dissimilarity between the at least two ultrasound frames, translating the two dimensional error matrix to an accumulated distance matrix, determining local minimum accumulated errors and global minimum accumulated errors from the accumulated distance matrix, and generating the delay waveform based on the determined local minimum accumulated errors and the global minimum accumulated errors.

Another embodiment of the present disclosure is directed to comparing samples of the at least two consecutive ultrasound frames to determine a phase change waveform between the at least two consecutive ultrasound frames. This includes determining a quadrature phase counterpart corresponding to each of the at least two ultrasound frames by applying Hilbert transform on the each of the at least two ultrasound frames, generating a single sideband (SSB) signal corresponding to each of the at least two ultrasound frames by adding the each of the at least two ultrasound frames to the corresponding quadrature phase counterpart, constructing continuous phase waveforms of each of the at least two ultrasound frames by performing a tangent inverse operation on the SSB signal corresponding to each of the at least two ultrasound frames, and determining the phase change waveform by subtracting the continuous phase waveforms of each of the at least two ultrasound frames.

Another embodiment of the present disclosure is directed to the at least two ultrasound frames including an equal number of samples.

Another embodiment of the present disclosure is directed to the at least two ultrasound frames including an unequal number of samples.

Embodiments of the present disclosure are directed to a vessel-wall-monitoring device for identifying boundaries of a blood vessel in a human body. The vessel-wall-monitoring device includes a memory storing ultrasound frames, a signal transceiver configured for receiving a plurality of ultrasound echo signals from an ultrasound transducer, wherein the plurality of ultrasound echo signals are transmitted to the ultrasound transducer from locations of the blood vessel, and a sample extractor and a controller that is communicatively connected to the sample extractor, the signal transceiver and the memory. The sample extractor is configured for continuously extracting at least two consecutive ultrasound frames from the plurality of ultrasound echo signals, and storing the at least two consecutive ultrasound frames in the memory. The controller is configured for comparing samples of the at least two consecutive ultrasound frames to determine at least one of a delay waveform and a phase change waveform between the at least two consecutive ultrasound frames, determining at least two adjacent extrema of at least one of the delay waveform and the phase change waveform, and identifying a proximal wall and a distal wall of the blood vessel based on the at least two adjacent extrema.

BRIEF DESCRIPTION OF FIGURES

Figure 1:
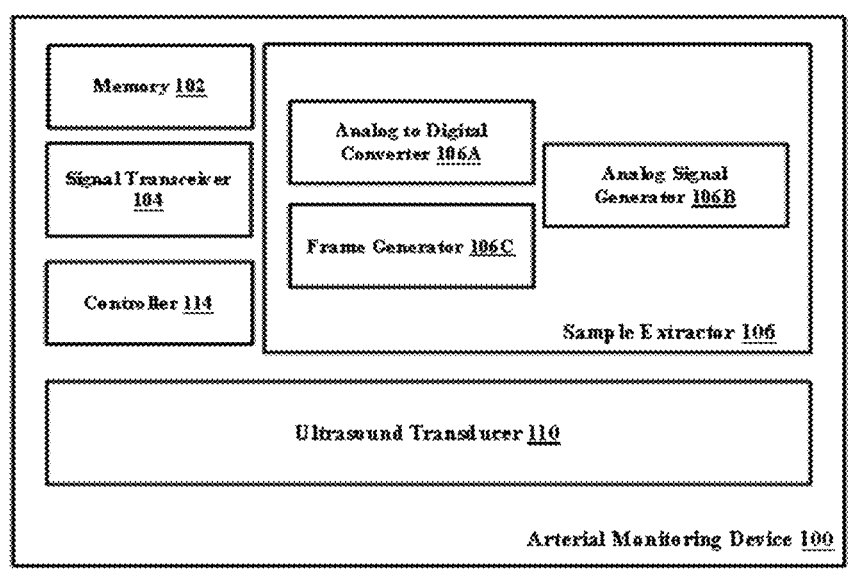
Figure 2:
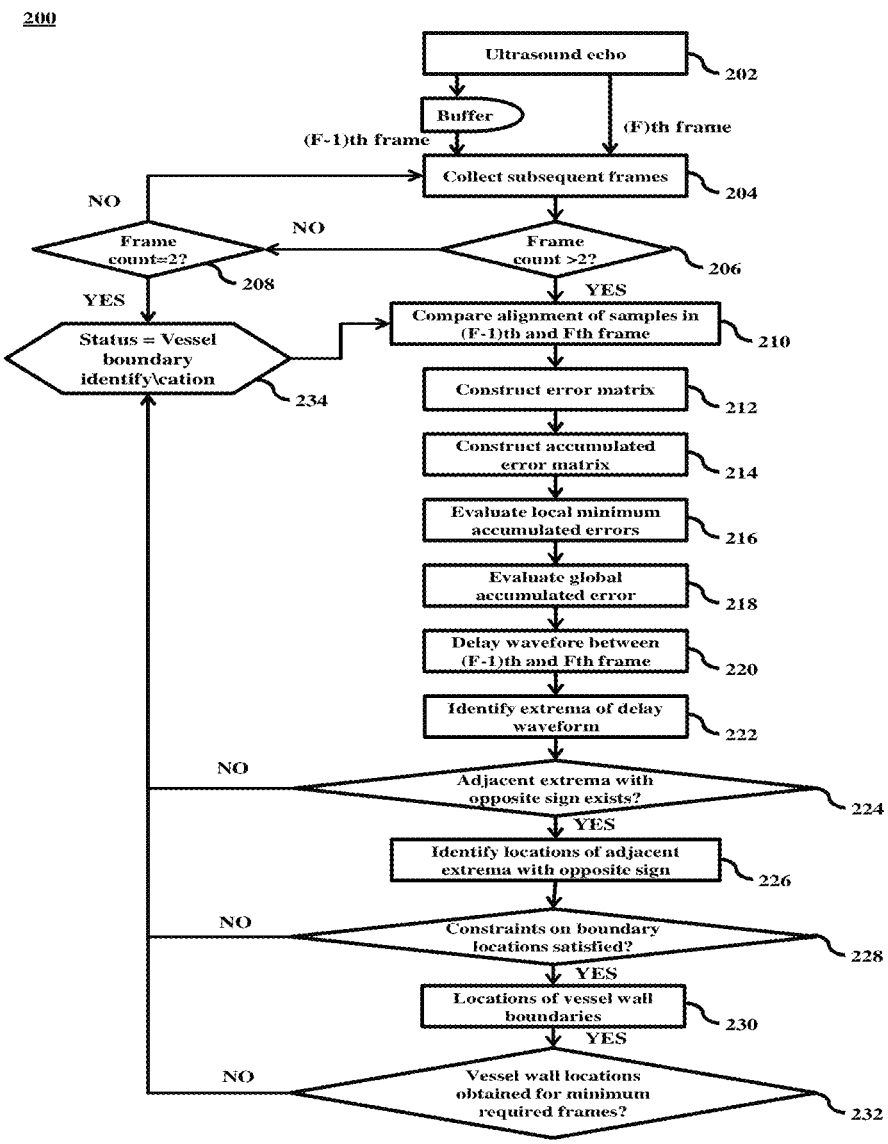
Figure 3:
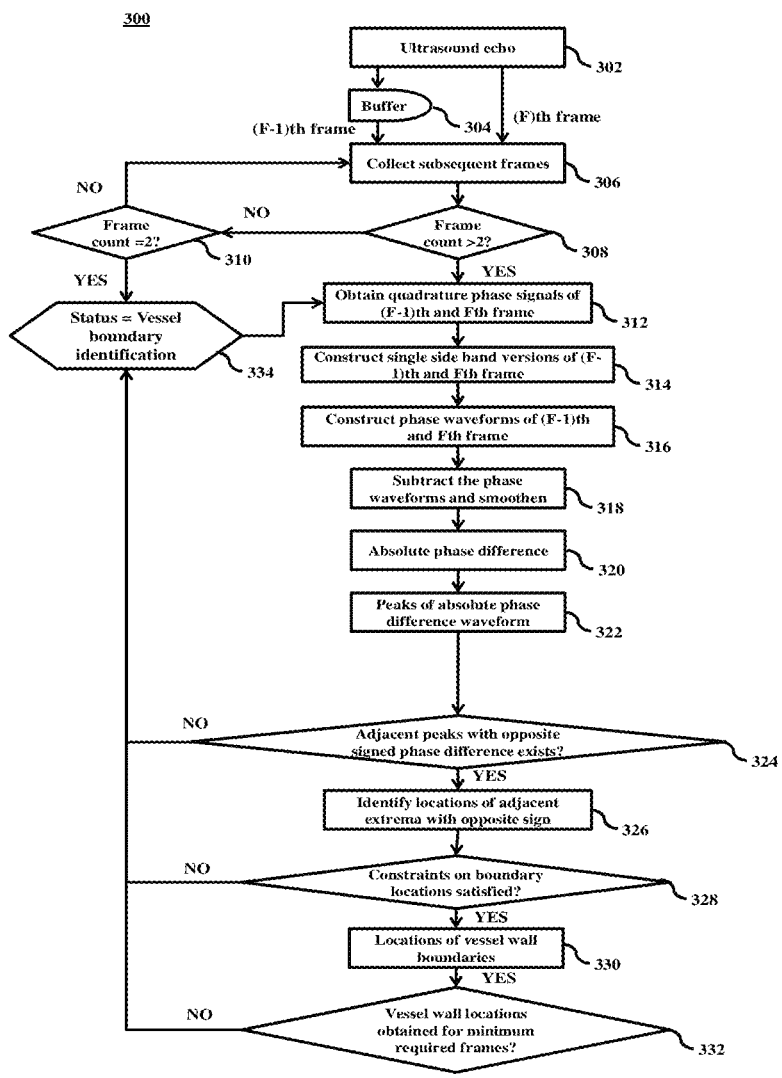
Figure 4:
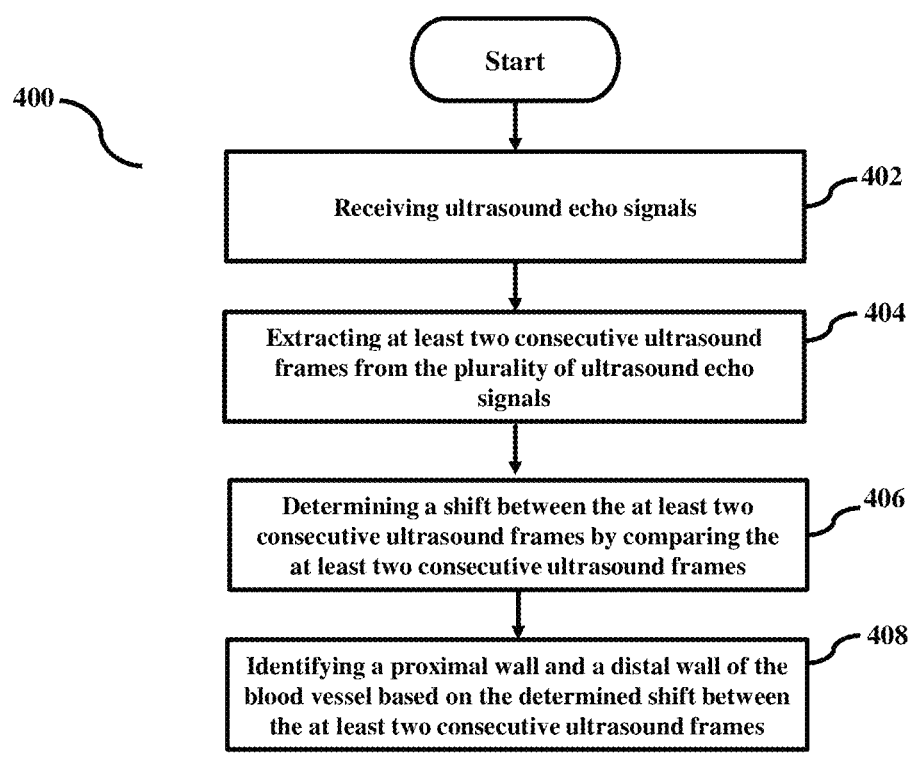
Figure 5:
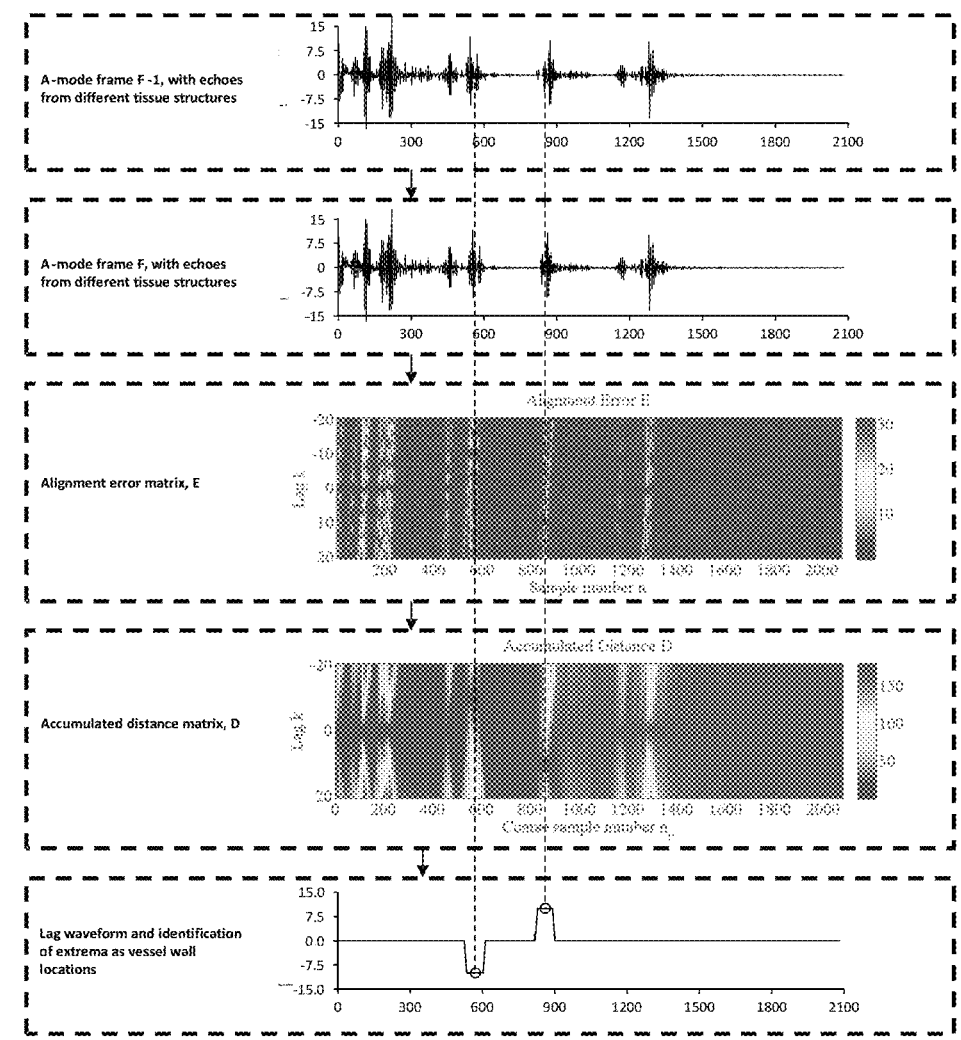
Figure 6:
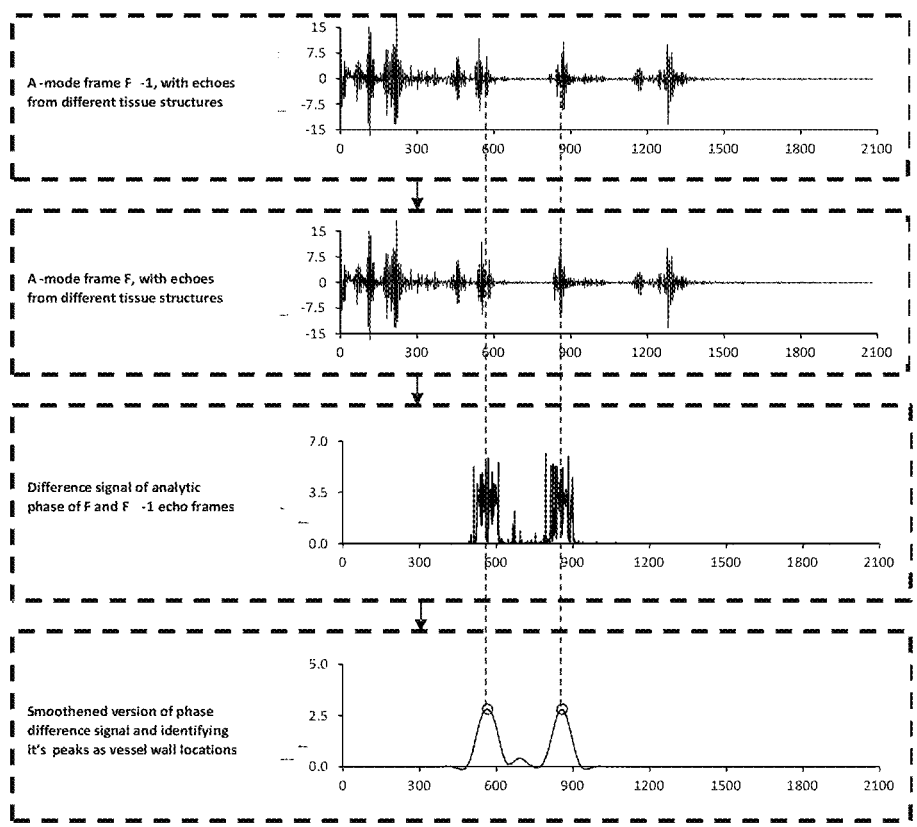

Having thus described the disclosure in general terms, reference will now be made to the accompanying figures, wherein:

FIG. 1 illustrates a vessel-wall-monitoring device for identifying boundaries of a blood vessel in a body, in accordance with various embodiments of the present disclosure;

FIG. 2 is a flow diagram illustrating a time domain method identifying boundaries of a vessel in a body using the vessel-wall-monitoring device, in accordance with various embodiments of the present disclosure;

FIG. 3 is a flow diagram illustrating a frequency domain method identifying boundaries of a vessel in a body using the vessel-wall-monitoring device, in accordance with various embodiments of the present disclosure;

FIG. 4 is a flow diagram illustrating a method of identifying a proximal wall and a distant wall of the blood vessel, in accordance with various embodiments of the present disclosure;

FIG. 5 is a set of intermediate-stage signal graphs illustrating the time domain method identifying boundaries of a vessel in a body using the vessel-wall-monitoring device, in accordance with various embodiments of the present disclosure; and FIG. 6 is a set of intermediate-stage signal graphs illustrating the frequency domain method identifying boundaries of a vessel in a body using the vessel-wall-monitoring device, in accordance with various embodiments of the present disclosure.

It should be noted that the accompanying figures are intended to present illustrations of exemplary embodiments of the present disclosure. These figures are not intended to limit the scope of the present disclosure. It should also be noted that accompanying figures are not necessarily drawn to scale.

DETAILED DESCRIPTION OF EMBODIMENT

Various embodiments of the present disclosure will now be described in detail with reference to the accompanying drawings. In the following description, specific details such as detailed configuration and components are merely provided to assist the overall understanding of these embodiments of the present disclosure. Therefore, it should be apparent to those skilled in the art that various changes and modifications of the embodiments described herein can be made without departing from the scope and spirit of the present disclosure. In addition, descriptions of well-known functions and constructions are omitted for clarity and conciseness.

Also, the various embodiments described herein are not necessarily mutually exclusive, as some embodiments can be combined with one or more other embodiments to form new embodiments. Herein, the term "or" as used herein, refers to a non-exclusive or, unless otherwise indicated. The examples used herein are intended merely to facilitate an understanding of ways in which the embodiments herein can be practiced and to further enable those skilled in the art to practice the embodiments herein. Accordingly, the examples should not be construed as limiting the scope of the embodiments herein. Further it should be possible to combine the flows specified in different figures to derive a new flow.

As is traditional in the field, embodiments may be described and illustrated in terms of blocks which carry out a described function or functions. These blocks, which may be referred to herein as managers, engines, controllers, units or modules or the like, are physically implemented by analog and/or digital circuits such as logic gates, integrated circuits, microprocessors, microcontrollers, memory circuits, passive electronic components, active electronic components, optical components, hardwired circuits and the like, and may optionally be driven by firmware and software. The circuits may, for example, be embodied in one or more semiconductor chips, or on substrate supports such as printed circuit boards and the like. The circuits constituting a block may be implemented by dedicated hardware, or by a processor (e.g., one or more programmed microprocessors and associated circuitry), or by a combination of dedicated hardware to perform some functions of the block and a processor to perform other functions of the block. Each block of the embodiments may be physically separated into two or more interacting and discrete blocks without departing from the scope of the disclosure. Likewise, the blocks of the embodiments may be physically combined into more complex blocks without departing from the scope of the disclosure.

The embodiments herein and the various features and advantageous details thereof are explained more fully with reference to the non-limiting embodiments that are illustrated in the accompanying drawings and detailed in the following description.

The embodiments disclosed herein can be implemented through at least one software program running on at least one hardware device and performing network management functions to control the elements. The elements shown in FIGS. 1-5 include blocks which can be at least one of a hardware device, or a combination of hardware device and software module.

In accordance with embodiments disclosed herein, document management involves acquiring any document and then retrieving document properties to map them to a pre-stored set of documents. Depending upon the document category, relevance of data inside document in any form such as text, QR code, etc. can be determined for providing services to the subject.

Reference in this specification to "one embodiment" or "an embodiment" means that a particular feature, structure, or characteristic described in connection with the embodiment is included in at least one embodiment of the present technology. The appearance of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described, which may be requirements for some embodiments but no other embodiments.

Moreover, although the following description contains many specifics for the purposes of illustration, anyone skilled in the art will appreciate that many variations and/or alterations to said details are within the scope of the present technology. Similarly, although many of the features of the present technology are described in terms of each other, or in conjunction with each other, one skilled in the art will appreciate that many of these features can be provided independently of other features. Accordingly, this description of the present technology is set forth without any loss of generality to, and without imposing limitations upon, the present technology.

FIG. 1 illustrates a vessel-wall-monitoring device 100 for identifying boundaries of a vessel. The vessel-wall-monitoring device 100 includes a memory 102, a signal transceiver 104, a sample extractor 106 and an ultrasound transducer 110. The transducer 110 can include an inbuilt (or external) transmitter and a receiver that transmit and receive ultrasound signals. While the generated ultrasound signal of the ultrasound transducer 110 propagates through a target site on a body, several ultrasound echoes are generated from various structures in the transmission path. These echoes are captured by the signal transceiver 104 and converted into signature analog waves using an analog signal generator 106B of the sample extractor 106. These analog signals are then processed with various signal conditioning elements, as desired using the frame generator 106C. These conditioned ultrasound analog signals are converted into digital signals using an analog to digital converter 106A and are stored temporarily in the memory 102. It is a continuous process and is controlled by a controller 114. The digitised ultrasound echo signals are transferred to the digital domain for further analyses and to perform various measurements by implementing aforesaid methods. Of note, an echo signal with a finite number of samples in the digital domain henceforth referred to as an ultrasound frame.

The ultrasound frames, acquired via the sample extractor 106, contain echoes formed from various tissue interfaces along the axis of the ultrasound scan. If the target artery vessel is situated along the scan line, the echoes formed from the boundaries of the artery appear to be shifting in each consecutive frame with a characteristic pattern. Typically, in the case of arteries, such boundaries can be named as proximal wall and distal wall of the artery. The proximal and distal walls would be moving in a direction opposite to each other. In the following paragraphs, two systematic methods, a time domain method and a frequency domain method, are described to locate and identify boundaries of the artery (viz. proximal wall and distal wall of the artery) by analysing the acquired ultrasound echo frames. It should be noted that, although the following method described in the context of an artery, is directly applicable to any vascular structure encompassing fluid with a characteristic motion.

In some embodiments, the electronic device 100 can include communication units pertaining to communication with remote computers, servers or remote databases over a communication network. The communication network can include a data network such as, but not restricted to, the Internet, local area network (LAN), wide area network (WAN), metropolitan area network (MAN) etc. In certain embodiments, the communication network can include a wireless network, such as, but not restricted to, a cellular network and may employ various technologies including enhanced data rates for global evolution (EDGE), general packet radio service (GPRS), global system for mobile communications (GSM), Internet protocol multimedia subsystem (IMS), universal mobile telecommunications system (UMTS) etc.

The controller 114 can be, but not restricted to, a Central Processing Unit (CPU), a microprocessor, or a microcontroller. The controller 114 executes sets of instructions stored on the memory 102.

The memory 102 includes storage locations to be addressable through the controller 114. The memory 102 is not limited to a volatile memory and/or a non-volatile memory. Further, the memory 102 can include one or more computer-readable storage media. The memory 102 can include non-volatile storage elements. For example, non-volatile storage elements can include magnetic hard discs, optical discs, floppy discs, flash memories, or forms of electrically programmable memories (EPROM) or electrically erasable and programmable (EEPROM) memories. In some embodiments, the memory 114 is communicably coupled to third party storage, cloud storage and the like.

In the time method 200 disclosed herein, as illustrated in FIG. 2, ultrasound frames are continuously collected and stored in a buffer (step 202 and step 204). Two consecutive frames, the current frame F and its previous frame (F−1) are used at a time, therefore the further process starts only after the frame count is greater than or equal to two (step 206 and step 208). Typically, both the $F^{th}$ and $(F-1)^{th}$ frames have an equal number of samples (N), else are made equal and then are compared (step 210). Then the alignment dissimilarity between these frames is measured by generating an error matrix (step 212). Since two consecutive frames are used, the error matrix is a two-dimensional matrix. The same operation can be performed with any desired number of successive frames, which results in an error matrix with the corresponding dimensionality.

Any $n^{th}$ column in the two-dimensional error matrix $E(k,n)$ is populated by comparing a sample at index n $F^{th}$ frame, with (2K+1) samples in (F−1)$^{th}$ frame, extracted using a window with its centre at the n$^{th}$ index of the frame (F−1). It can be compared in any form such as, but not limited to, algebraic or logical. For example, the samples are compared using an 'absolute difference operator' in Equation (1) and the description that follows. This comparison operation is performed for all the samples in the F$^{th}$ frame ($S_1$ signal) by correspondingly shifting the window centre in the (F−1)$^{th}$ frame ($S_2$ signal). Subsequently, there are N columns in error matrix E(k,n) with each column consisting of (2K+1) samples. Here, k represents the lags from the selected windows' centre index in (F−1)$^{th}$ frame from which the samples are extracted for comparison against one sample extracted from the F$^{th}$ frame. In each column of E(k,n) the indices of minima represent the lags that align the samples in F$^{th}$ frame with the samples in (F−1)$^{th}$ frame.

$$E(k,n)=|S_1(n)-S_2(n-k)|; n=[1,N] \text{ and } k=[-K,K] \quad (1)$$

Once the error matrix E(k,n) is derived, it is translated to an 'accumulated error matrix' D(k,n) as a representation of the cumulative errors while traversing across the length of the frame via a various lag path (step 214). However not constrained to, the first column of D(k,n) is initialised as the first column of E(k,n) as:

$$D(k,1)=E(k,1). \quad (2)$$

From the second column to the N$^{th}$, elements of D(k,n) in a k$^{th}$ row and n$^{th}$ column are obtained by adding the element in E(k,n) corresponding to the k$^{th}$ row and n$^{th}$ column with the smallest of the elements extracted from (k−1)$^{th}$, k$^{th}$ and (k+1)$^{th}$ rows in the (n−1)$^{th}$ column, as shown in Equation (3);

$$D(k, n) = E(k, n) + \min\begin{cases} D(k-1, n-1) \\ D(k, n-1), n = 2, 3, \dots N \\ D(k+1, n-1) \end{cases} \quad (3)$$

This form of generating accumulated error matrix process iteratively adds the minimum of the adjoining elements presents one column apart. Now the 'local minimum accumulated errors' are computed by traversing in the reverse direction, that is from N$^{th}$ column to 1$^{st}$ column of D(k,n) (step 216). As such, the local minimum errors for N columns yields L(n) matrix, which represents the delay waveform between frames F and (F−1) that minimizes the global error (step 216, step 218, and step 220). The procedure of construction of L(n) involves, however not constrained, initialising the lag corresponding to the minimum of the last column elements in D(k,n) as L(N);

$$L(N)=\arg(\min D(k,N)), \forall k. \quad (4)$$

The other elements of the matrix L(n) are to be estimated for n=N−1 to 1. For this, the elements from any column n corresponding to lags L(n+1)−1, L(n+1) and L(n+1)+1 are collected, and the lag corresponding to the minimum of these elements is assigned to L(n), as give below.

$$L(n)=\arg(\min D(k,n)), \text{ for, } k \in [L(n+1)+1, L(n+1), L(n+1)-1]$$

$$\text{and } n=N-1, N-2, \dots 1 \quad (5)$$

Therefore, the sub-paths yielding local minimum accumulated errors when sequentially connected, it constructs the complete path estimating L(n) and producing a 'global minimum accumulated error.' (step 216, step 218, and step 220)

In another embodiment, for more robust evaluation of delay waveform L(n), a modified D(k,n) matrix construction can also be adopted. In this approach, instead of constructing D(k,n) for all the columns (n=1: N), it is constructed for columns that are spaced m positions apart. Therefore, the constructed accumulated error matrix' D(k,i), where i=1:m: N, consists of only N/m columns. Here, the first column of D(k,i) is initialised as the first column of E(k,n). Further, for the columns (i=2:N/m), any element of D(k,i) in row k and column i is evaluated by first identifying (2m+1) paths that connect the element of E(k,n) in row k and column i*m to the elements in column (i−1)*m and rows (k−m):(k+m). These elements in E(k,n) along the individual paths are added to obtain (2m+1) such path summations and the minimum of these summation values corresponding to a particular path is added to the element of E(k,n) in the k$^{th}$ row and (i*m)$^{th}$ column. This value is assigned to the element of D(k,i) in the k$^{th}$ row and i$^{th}$ column.

Once the delay waveforms are derived (step 220), its prominent extrema (local maxima and minima) are then identified (step 222). From the start of the delay waveform to the last extrema, adjacent ones are selected in pair (step 224) and analysed for the direction and magnitude of the corresponding delay. If there are any adjacent pair of extrema with delay values with opposite signs (that is a local maxima followed by local minima or vice versa), and have magnitude above a set threshold level, their locations are identified as the boundaries of the arterial vessel (the proximal and distal wall boundaries) (step 224 and step 226). It may be noted that the selection of extrema with opposite signs is applicable in the context of an artery or tubular structures following similar out-of-phase characteristic wall motions. However, the aforesaid technique is equally amenable for various structures with respective characteristic motion.

In the context of an artery, the method 200 imposes other constraints to validate the identified wall boundaries, which include the set threshold for the minimum location of the proximal wall, and the threshold for minimum and maximum differences between the identified boundaries (step 228 and step 230). If none of the pairs of extrema meets these criteria, this implies that the walls are not identified in frames F and (F−1). In the next iteration, these frames are updated with the latest, and the procedure is repeated until the wall boundaries are identified for a sufficient number of set consecutive iterations (step 232 and step 234).

In the frequency method 300 disclosed herein, as described in FIG. 3, ultrasound frames are continuously collected (step 302 and step 306) and stored in a temporary buffer (step 304). Two consecutive frames, the current frame F and its previous frame (F−1) are used at a time, therefore the further process starts only after the frame count is greater than or equal to two (step 308 and step 310). Typically, both F$^{th}$ and (F−1)$^{th}$ frame have an equal number of samples (N), else make them equal. Initially, a Hilbert transform operation is applied on the F$^{th}$ and (F−1)$^{th}$ frame which yields their respective quadrature-phase counterpart (step 312). By adding the original frames (F and (F−1)) with their quadrature versions, G and (G−1), respectively single-sideband (SSB) signals are generated (step 314). From the obtained SSB signals, the continuous phase waveforms of the frames (Φ) are constructed by performing a tangent inverse operation on the ratio of the imaginary component to the real component (316). That is, the phase waveform of F$^{th}$ and (F−1)$^{th}$ frames, denoted Φ(F) and Φ((F−1)), are generated as given in Equation 6 and Equation 7.

$$\Phi(F) = \tan^{-1}\left(\frac{G}{F}\right) \quad (6)$$

$$\Phi((F-1)) = \tan^{-1}\left(\frac{(G-1)}{(F-1)}\right) \quad (7)$$

Since the acquired echoes are in the form of Gaussian modulated sinusoids, their phase oscillates between $-\pi$ to $\pi$, the principle phase value. The change in phase ($\Delta\Phi$) of the entire echo signal from $F^{th}$ to $(F-1)^{th}$ frame is evaluated by subtracting $\Phi(F)$ and $\Phi((F-1))$ and then smoothened (step 318). The absolute of the $\Delta\Phi$ waveform represents the magnitude of the phase changes in echoes corresponding to various structures encompassed in the captured frame (step 320). This $\Delta\Phi$ waveform is smoothened with a suitable tool such as (though not restricted to) a moving window average filter or a low-pass filter or a median filter (step 318). Once the smooth absolute $\Delta\Phi$ waveform is constructed, its extrema (strong peaks) are identified (step 322). From start to end of the signal, the adjacent pair of strong peaks are selected, and the sign of $\Delta\Phi$ value at those peaks are inspected (step 324). Then, the adjacent pair of smooth $\Delta\Phi$ peaks with values exhibiting opposite sign is identified (step 326). The locations of these peaks (in the smooth $\Delta\Phi$ waveform) are the locations of the proximal and distal wall echoes in the corresponding frame; hence, the boundaries of the arterial vessel (step 330).

To improve the robustness of the vessel boundary identification method alluded above, a set of constraints are enforced in the context of arterial vessels (step 328 and step 332). The constraints include: (1) the proximal wall location should be greater than the enforced minimum criteria, and (2) the difference between the locations of the proximal and distal wall echoes should be within a specified range. These are subjective to the target artery being scanned or are refined based on the structure being analysed. These constraints should accordingly be modified (if required) while implementing the proposed method for different vascular or tubular structures. If none of the smooth $\Delta\Phi$ peak pairs meets aforesaid criteria, which implies the walls are not identified in $F^{th}$ and $(F-1)^{th}$ frames. In the next iteration, these frames are updated with the latest, and the procedure is repeated until the walls are identified for a sufficient number of set consecutive iterations (step 334). Since real-time visual feedback is available for the operator, the position and orientation of the scanning element can be precisely adjusted towards the walls of the target vessel.

FIG. 4 is a flow diagram (400), illustrating the method of identifying the proximal wall and the distal wall of the blood vessel in the human body, according to an embodiment as disclosed herein.

As seen in FIG. 4, At 402, the method comprises receiving ultrasound echo signals from the transducer by the vessel-wall-monitoring device (100) from different location of the blood vessel.

At 404, the method comprises continuously extracting, by the vessel-wall-monitoring device (100), at least two consecutive ultrasound frames from the ultrasound echo signals. Samples of the at least two consecutive ultrasound frames are compared to determine the alignment dissimilarity between the at least two ultrasound frames and the two dimensional alignment error matrix is generated. Further the two dimensional error matrix is translated to the accumulated distance matrix for determining local minimum accumulated. Finally the delay waveform is generated based on the path that connects the determined local minimum accumulated errors which yields the global minimum accumulated errors.

In an embodiment the quadrature phase counterpart is determined corresponding to each of the at least two ultrasound frames by applying Hilbert transform on the each of the at least two ultrasound frames. SSB signal is generated corresponding to each of the at least two ultrasound frames by adding the each of the at least two ultrasound frames to the corresponding quadrature phase counterpart. Further continuous phase waveforms of each of the at least two ultrasound frames are constructed by performing the tangent inverse operation on the SSB signal corresponding to each of the at least two ultrasound frames. Finally the phase change waveform is determined by subtracting the continuous phase waveforms of each of the at least two ultrasound frames.

At 406, the method includes determining, by the vessel-wall-monitoring device (100), a shift between the at least two consecutive ultrasound frames by comparing the at least two consecutive ultrasound frames. In an embodiment determining the shift comprises determining the delay waveform and the phase change waveform.

At 408, the method includes identifying, by the vessel-wall-monitoring device (100), a proximal wall and a distal wall of the blood vessel based on the determined shift between the at least two consecutive ultrasound frames.

FIG. 5 is a set of intermediate-stage signal graphs 500 illustrating the time domain method identifying boundaries of a vessel in a body using the vessel-wall-monitoring device, in accordance with various embodiments of the present disclosure. As shown in FIG. 5, wall echo peaks of the $F^{th}$ and $(F-1)^{th}$ frames, coincide with extrema of the delay waveform (indicated as lag waveform in the last row). Any $n^{th}$ column in the two-dimensional error matrix E(k,n) is populated by comparing a sample at index n in $F^{th}$ frame, with (2K+1) samples in $(F-1)^{th}$ frame, extracted using a window with its centre at the $n^{th}$ index of the frame (F-1). The error matrix E(k,n) is translated to an 'accumulated error matrix' D(k,n) as a representation of the cumulative errors while traversing across the length of the frame via a various lag path. Finally delay waveforms are generated in which the extrema are identified as shown in FIG. 4 to identify the walls of the vessel.

FIG. 6 is a set of intermediate-stage signal graphs 600 illustrating the frequency domain method identifying boundaries of a vessel in a body using the vessel-wall-monitoring device, in accordance with various embodiments of the present disclosure. As shown in FIG. 6, wall echo peaks of the $F^{th}$ and $(F-1)^{th}$ frames, coincide with extrema of the smoothened phase change waveform (indicated in the last row). Two consecutive frames, the current frame F and its previous frame (F-1), are used at a time. Typically, both $F^{th}$ and $(F-1)^{th}$ frame have an equal number of samples (N), else make them equal. Initially, a Hilbert transform operation is applied on the $F^{th}$ and $(F-1)^{th}$ frame which yields their respective quadrature-phase counterpart. By adding the original frames (F and (F-1)) with their quadrature versions, G and (G-1), respectively single-sideband (SSB) signals are generated. From the obtained SSB signals, the continuous phase waveforms of the frames ($\Phi$) are constructed by performing a tangent inverse operation on the ratio of the imaginary component to the real component. The change in phase ($\Delta\Phi$) of the entire echo signal from $F^{th}$ to $(F-1)^{th}$ frame is evaluated by subtracting $\Phi(F)$ and $\Phi((F-1))$. The absolute of the $\Delta\Phi$ waveform represents the magnitude of the phase changes in echoes corresponding to various structures encompassed in the captured frame. This ΔΦ waveform is smoothened with a suitable tool such as (though not restricted to) a moving window average filter or a low-pass filter or a median filter. Once the smooth absolute ΔΦ waveform is constructed, its extrema (strong peaks) are identified as the locations of the proximal and distal wall echoes in the corresponding frame; hence, the boundaries of the arterial vessel.

The foregoing descriptions of specific embodiments of the present technology have been presented for purposes of illustration and description. They are not intended to be exhaustive or to limit the present technology to the precise forms disclosed, and obviously, many modifications and variations are possible in light of the above teaching. The embodiments were chosen and described in order to best explain the principles of the present technology and its practical application, to thereby enable others skilled in the art to best utilise the present technology and various embodiments with various modifications as are suited to the particular use contemplated. It is understood that various omissions and substitutions of equivalents are contemplated as circumstance may suggest or render expedient, but such are intended to cover the application or implementation without departing from the spirit or scope of the claims of the present technology.

While several possible embodiments of the invention have been described above and illustrated in some cases, it should be interpreted and understood as to have been presented only by way of illustration and example, but not by limitation. Thus, the breadth and scope of a preferred embodiment should not be limited by any of the above-described exemplary embodiments.

We claim:

1. A method for identifying boundaries of a blood vessel in a human body, the method comprising:
    receiving, by a vessel-wall-monitoring device (100), a plurality of ultrasound echo signals comprising a plurality of ultrasound frames from an ultrasound transducer (110), wherein the plurality of ultrasound echo signals are transmitted to the ultrasound transducer (110) from locations of the blood vessel;
    extracting, by the vessel-wall-monitoring device (100), at least two consecutive ultrasound frames from the plurality of ultrasound echo signals;
    determining, by the vessel-wall-monitoring device (100), a shift between the at least two consecutive ultrasound frames by comparing the at least two consecutive ultrasound frames, wherein comparing the at least two consecutive ultrasound frames is used to determine a phase change waveform between the at least two consecutive ultrasound frames, determining the phase change waveform comprises:
        determining a quadrature phase counterpart corresponding to each of the at least two consecutive ultrasound frames by applying Hilbert transform on the each of the at least two ultrasound frames,
        generating a single sideband (SSB) signal corresponding to each of the at least two ultrasound frames by adding the each of the at least two consecutive ultrasound frames to the corresponding quadrature phase counterpart,
        constructing continuous phase waveforms of each of the at least two consecutive ultrasound frames by performing a tangent inverse operation on the SSB signal corresponding to each of the at least two consecutive ultrasound frames, and
        determining the phase change waveform by subtracting the continuous phase waveforms of each of the at least two ultrasound frames; and
    identifying, by the vessel-wall-monitoring device (100), the boundaries of the blood vessel, wherein identifying the boundaries comprises identifying a proximal wall and a distal wall of the blood vessel based on the determined shift between the at least two consecutive ultrasound frames.

2. The method as claimed in claim 1, wherein the at least two consecutive ultrasound frames are digitized data frames of the plurality of ultrasound echo signals with a finite number of samples.

3. The method as claimed in claim 1, wherein the proximal wall and the distal wall of the blood vessel move in opposite directions.

4. The method as claimed in claim 1, wherein determining the shift comprises determining a delay wave form and the phase change waveform between the at least two consecutive ultrasound frames.

5. The method as claimed in claim 4, wherein comparing the at least two consecutive ultrasound frames to determine the delay waveform between the at least two consecutive ultrasound frames comprises:
    comparing samples of the at least two consecutive ultrasound frames to determine an alignment dissimilarity between the at least two ultrasound frames;
    generating a two-dimensional alignment error matrix based on the alignment dissimilarity between the at least two ultrasound frames;
    translating the two-dimensional error matrix to an accumulated distance matrix;
    determining local minimum accumulated errors from the accumulated distance matrix; and
    generating the delay waveform based on a path that connects the determined local minimum accumulated errors which yields global minimum accumulated errors.

6. The method as claimed in claim 1, wherein identifying the proximal wall and the distal wall of the blood vessel comprises determining at least two adjacent extrema of at least one of a delay waveform and the phase change waveform and determining the at least two adjacent extrema to have opposing signs and magnitudes of the at least two adjacent extrema to be above a predefined threshold.

7. The method as claimed in claim 1, wherein the ultrasound frames comprise an equal number of samples.

8. The method as claimed in claim 1, wherein the ultrasound frames comprise an unequal number of samples.

9. A vessel-wall-monitoring device (100) for identifying boundaries of a blood vessel in a human body, the vessel-wall-monitoring device (100) comprising:
    a memory (102) storing ultrasound frames;
    an ultrasound transducer (110);
    a signal transceiver (104) configured for receiving a plurality of ultrasound echo signals comprising a plurality of ultrasound frames from the ultrasound transducer (110), wherein the plurality of ultrasound echo signals are transmitted to the ultrasound transducer (110) from the blood vessel;
    a sample extractor (106) communicatively coupled to the signal transceiver (104) and the memory (102), configured for:
        extracting at least two consecutive ultrasound frames from the plurality of ultrasound echo signals, and storing the at least two consecutive ultrasound frames in the memory;

a controller (114) communicatively connected to the sample extractor, the signal transceiver and the memory, configured for:
  determining a shift between the at least two consecutive ultrasound frames by comparing samples of the at least two consecutive ultrasound frames, wherein comparing the at least two consecutive ultrasound frames is used to determine a phase change waveform between the at least two consecutive ultrasound frames, determining the phase change waveform comprises:
    determining a quadrature phase counterpart corresponding to each of the at least two ultrasound frames by applying Hilbert transform on the each of the at least two consecutive ultrasound frames,
    generating a single sideband (SSB) signal corresponding to each of the at least two consecutive ultrasound frames by adding the each of the at least two ultrasound frames to the corresponding quadrature phase counterpart,
    constructing continuous phase waveforms of each of the at least two consecutive ultrasound frames by performing a tangent inverse operation on the SSB signal corresponding to each of the at least two ultrasound frames, and
    determining the phase change waveform by subtracting the continuous phase waveforms of each of the at least two consecutive ultrasound frames; and
  identifying the boundaries of the blood vessel, wherein identifying the boundaries comprises identifying a proximal wall and a distal wall of the blood vessel based on the shift between the at least two consecutive ultrasound frames.

10. The vessel-wall-monitoring device (100) as claimed in claim 9, wherein the at least two consecutive ultrasound frames are digitized data frames of the plurality of ultrasound echo signals with a finite number of samples.

11. The vessel-wall-monitoring device (100) as claimed in claim 9, wherein the proximal wall and the distal wall of the blood vessel of a subject move in opposite directions.

12. The vessel-wall-monitoring device (100) as claimed in claim 9, wherein determining the shift comprises determining a delay waveform and the phase change waveform between the at least two consecutive ultrasound frames.

13. The vessel-wall-monitoring device (100) as claimed in claim 12, wherein comparing samples of the at least two consecutive ultrasound frames to determine the delay waveform between the at least two consecutive ultrasound frames comprises:
  comparing samples of the at least two consecutive ultrasound frames to determine an alignment dissimilarity between the at least two ultrasound frames;
  generating a two dimensional alignment error matrix based on the alignment dissimilarity between the at least two ultrasound frames;
  translating the two dimensional error matrix to an accumulated distance matrix;
  determining local minimum accumulated errors from the accumulated distance matrix; and
  generating the delay waveform based on a path that connects the determined local minimum accumulated errors which yields global minimum accumulated errors.

14. The vessel-wall-monitoring device (100) as claimed in claim 9, wherein identifying the proximal wall and the distal wall of the blood vessel based on adjacent extrema comprises determining at least two adjacent extrema of at least one of a delay waveform and the phase change waveform and determining the at least two adjacent extrema to have opposing signs and magnitudes of the at least two adjacent extrema to be above a predefined threshold.

15. The vessel-wall-monitoring device (100) as claimed in claim 9, wherein the at least two ultrasound frames comprise an equal number of samples.

16. The vessel-wall-monitoring device (100) as claimed in claim 9, wherein the at least two ultrasound frames comprise an unequal number of samples.

* * * * *